United States Patent
Doucha et al.

[11] Patent Number: 5,981,271
[45] Date of Patent: *Nov. 9, 1999

[54] PROCESS OF OUTDOOR THIN-LAYER CULTIVATION OF MICROALGAE AND BLUE-GREEN ALGAE AND BIOREACTOR FOR PERFORMING THE PROCESS

[75] Inventors: Jiri Doucha, Trebon; Karel Livansky, Ceska republika, both of Czech Rep.

[73] Assignee: Mikrobiologicky Ustav Akademie Ved Ceske Republiky, Prague, Czech Rep.

[ * ] Notice: This patent issued on a continued prosecution application filed under 37 CFR 1.53(d), and is subject to the twenty year patent term provisions of 35 U.S.C. 154(a)(2).

[21] Appl. No.: 08/963,339

[22] Filed: Nov. 3, 1997

[30] Foreign Application Priority Data

Nov. 6, 1996 [CZ] Czech Rep. ............................ 3266-96

[51] Int. Cl.$^6$ .............................. C12M 1/14; C12N 1/12
[52] U.S. Cl. .................................... 435/292.1; 435/257.1; 435/257.3; 47/1.4
[58] Field of Search ............................. 435/257.1, 257.3, 435/292.1; 47/1.4

[56] References Cited

U.S. PATENT DOCUMENTS 3,468,057  9/1969  Buisson et al. ..................... 435/292.1
5,541,056  7/1996  Huntley et al. ..................... 435/292.1

FOREIGN PATENT DOCUMENTS 279579    5/1995   Czech Rep. .
278213    6/1993   Czechoslovakia .
2596412  10/1987   France ................................ 435/292.1
5-284958 11/1993   Japan ................................. 435/292.1
2118572  11/1983   United Kingdom ................ 435/292.1

*Primary Examiner*—William H. Beisner
*Attorney, Agent, or Firm*—Notaro & Michalos P.C.

[57] ABSTRACT

Process of outdoor thin-layer cultivation of algae in which suspension of algae saturated with carbon dioxide and enriched with necessary nutrients, is distributed on inclined cultivation areas where the suspension of algae is distributed on inclined cultivation areas under turbulent flow which depends on velocity of flow, on coefficient of roughness of the cultivation surfaces, on the thickness of the algal suspension layer and on inclination of the cultivation surface. Between individual cultivation areas carbon dioxide is supplied into the suspension and the suspension flowing from the lowest cultivation area is conveyed into the collecting tank from which it is pumped on the upper edge of the highest cultivation area. Bioreactor for accomplishing the mentioned process is composed of at least two individual cultivation meandering areas (1a, 1b, 1c, 1d) where the lower end of the upper area and the beginning of the next lower area, inclined in the opposite direction, are connected by channels (2) in which outlets for supply of carbon dioxide into suspension are placed.

9 Claims, 1 Drawing Sheet

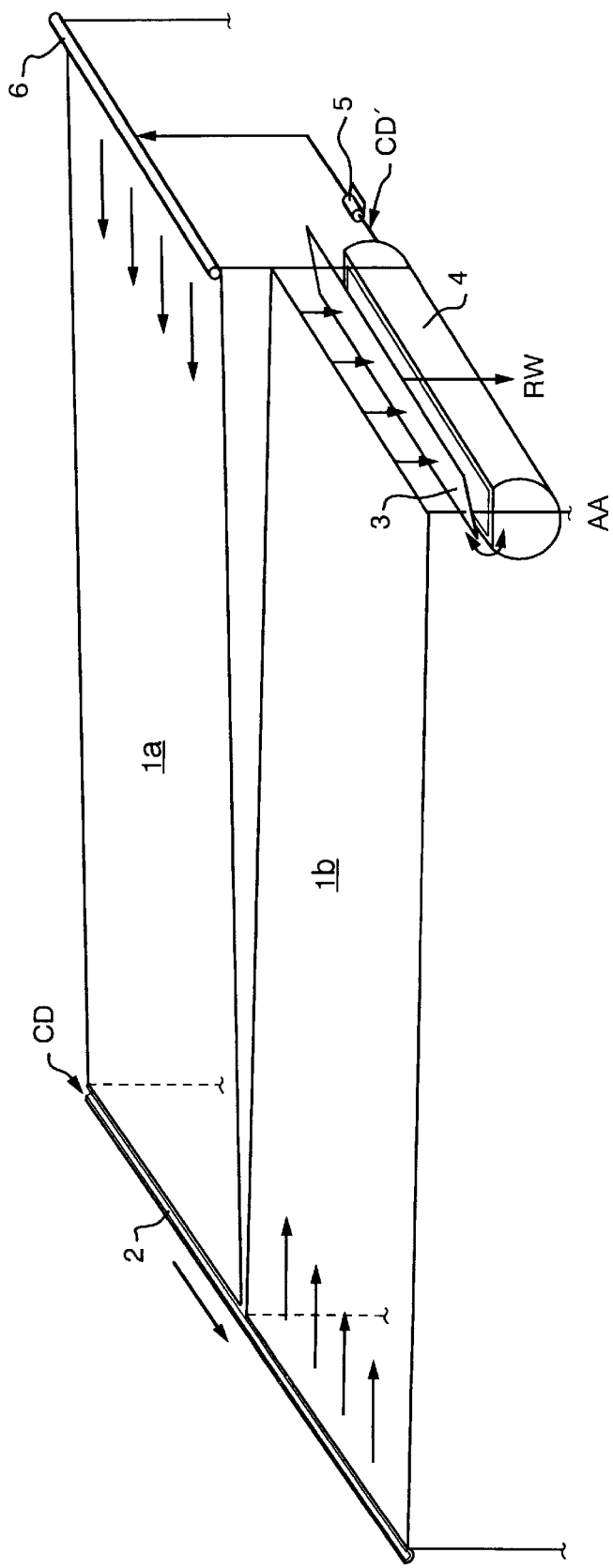

PROCESS OF OUTDOOR THIN-LAYER CULTIVATION OF MICROALGAE AND BLUE-GREEN ALGAE AND BIOREACTOR FOR PERFORMING THE PROCESS

FIELD OF TECHNIQUE

The patent describes the process of outdoor thin-layer cultivation of algae and blue-green algae (further only algae), in which suspension of algae saturated with carbon dioxide and enriched with necessary nutrients is distributed on inclined cultivation areas. Besides, the patent describes a bioreactor for performing the mentioned process.

PRESENT STATE OF TECHNIQUE

Outdoor cultivation of algae and blue-green algae is performed mostly in 4–8 m wide horizontal channels having a form of elongated ellipse (raceway ponds), in which 15–30 cm thick layer of inorganic nutrient solution with algae bubbled through by carbon dioxide, is continuously moved, most often by means of paddle-wheels, at velocity of 15–30 $cm.s^{-1}$ (Stengel, Ber. Deutsch. Bot. Ges., Bd. 83, Heft 11, 1970, 589–606; Goldman, Water Res. 13, 1979, 1–19; Richmond and Becker, CRC Handbook of Microalgal Mass Culture, CRC Press, Boca Raton, Fla., 1986, 245–253; Oswald, Microalgal Biotechnology, Cambridge U.P., 1988, 357–394; Becker, Microalgal Biotechnology, Cambridge U.P., 1994, 293 pp). The main drawback of this system is the low concentration of algae which due to the utilization of light should not be higher than 500 mg dry weight per 1 liter of nutrient solution. Slow flow of lower suspension layer can cause sedimentation of algae at the bottom of the channel. The laminar and relatively slow flow of the suspension results in inefficient utilization of light in the upper layer of light-oversaturated algae and leads to accumulation of oxygen dissolved in the suspension. High $O_2$ concentration inhibits photosynthesis and increases photorespiration of algae. The efficiency of saturation of the suspension with carbon dioxide by means of bubbling is very low (it does not exceeded 30%). The circulation of the suspension is continuous (day and night) and is an energy-demanding process. Highly energy-demanding is also the separation of algae from the nutrient solution at the harvest of algae.

The above-mentioned shortcomings are partly eliminated by the system, in which the algal suspension flows down an inclined surface of 3% slope. Perpendicularly to the flow at 15 cm distances there are placed slanted baffles 4 cm high, with 5 mm high slots between the cultivation surface and the baffles. The suspension flowing over and under the baffles is intensively mixed and, besides, baffles make it possible to keep the required thickness (5 cm) of algal layer over the whole cultivation area. The suspension flowing down the one-sided inclined cultivation area is being returned unilluminated by a collecting pipe into a pump which again delivers the suspension to the upper edge of the inclined cultivation area (Šetlík et al., Algolog. Stud. J, 1970, 111–164). The circulation takes place during the day, at night the suspension is kept in an aerated tank. Saturation of the suspension with carbon dioxide is performed by dispersing the suspension into a space inside a pressure vessel with a high concentration of gaseous $CO_2$. This system has the following disadvantages; about 20% of the suspension in the collecting channel and returning pipe is being permanently in the dark, furthermore, a relatively high energy consumption is needed for the operation of the pump and for aeration of the suspension kept in the tank between the cultivation periods, and the installation of baffles at the beginning of each culture season and maintenance (washing) of the cultivation surface is laborious.

PRINCIPLE OF THE INVENTION

The subject of the patent is the process of outdoor thin-layer cultivation of algae and blue-green algae (further only algae) in which suspension of algae, saturated with carbon dioxide and enriched with necessary nutrients, is distributed on inclined cultivation areas, where, according to the patent, the suspension of algae is distributed on inclined cultivation areas under turbulent flow which depends on the inclination of the cultivation areas, on the coefficient of roughness of the cultivation surfaces, on the thickness of the algal suspension layer and on the velocity of flow. The velocity of flow of the algal suspension is preferably 30–150 $cm.s^{-1}$, the coefficient of roughness of the inclined surfaces $n=0.005-0.150$ $m^{-1/3}.s$, the inclination of the area is 1.1–2.5% and the thickness of the suspension layer is 5–18 mm. Intensive turbulence optimizes the change of light and dark periods of individual cells resulting in a high efficiency of light utilization. Saturation of the suspension with carbon dioxide is performed between individual inclined cultivation areas in connecting channels in which carbon dioxide is enclosed in a space formed by the connecting channel and the algal suspension overflowing from the inclined cultivation area into the collecting channel. In order to increase the concentration of carbon dioxide in the algal suspension, it may be advantageous to supply $CO_2$ into the suction pipe of the recirculation pump. Part of the patent is the process of removal of oxygen dissolved in the suspension which evolves during photosynthesis, when the algal suspension is being diffused during its flow into the collecting tank. In such a way, the concentration of oxygen decreases close to the $O_2$ concentration in ambient air. The high concentration of oxygen in the suspension of algae inhibits the growth rate and production of algae.

The bioreactor for accomplishing the mentioned process consists of at least one module, which is composed of at least two individual inclined cultivation areas arranged in a meandering way, where the lower end of the upper area and the beginning of the next lower area, inclined in an opposite direction, are connected by channels through which the suspension flows from the upper area to the lower area, and where outlets for the supply of the suspension with carbon dioxide are placed. Below the end of the lowest-inclined cultivation area a collecting tank is placed which is connected through a pump with the upper edge of the highest-inclined cultivation area. Between the end of the lowest cultivation area and the collecting tank can be placed preferably a diffusing area which, if needed, serves also for draining off rain water. The total length of the culture area down which the suspension flows is given by the number of individual cultivation areas and by the sum of their lenghts. The long path of suspension flow compared to its width brings important savings of energy necessary for pumping the suspension from the lowest point to the upper distributing edge of the cultivation area.

By the process according to the patent, the energy input needed for the circulation of the suspension and for separation of biomass at harvesting, is reduced to less than 10% compared to the classical system of raceway ponds, and to 30% compared to the original system of inclined areas, and the unit productivity of algae rises by about 25%, which makes it possible to growth the algae to high harvesting concentrations.

EXAMPLES OF PATTENT FEASIBILITY

In the following description the patent is elucidated in more detail in examples and figures, in which two variants of the module of the bioreactor according to the patent are depicted. The module in the FIGURE consists of two individual inclined cultivation areas, arranged in a meandering way, which are mutually connected by channels in which outlets for supply of carbon dioxide (not depicted) are placed.

EXAMPLE

Bioreactor according to the FIGURE consists of one module composed of two meandering inclined cultivation areas 1a, 1b, where the lower end of the higher area 1a and the beginning of the lower area 1b, inclined in the opposite direction, are connected by channels 2. In channels 2 are placed outlets for saturation of the suspension with carbon dioxide, supplied by means of pipe CD. These outlets are preferably formed by perforated tubes made of plastic materials. Below the end of the lower cultivation are 1b is placed the collecting tank 4 while a diffusing area 3 located between it and the end of the lower cultivation area 1b serves for collecting rain water which is then taken off by drain RW into a discharge. Collecting tank 4 is connected through pump 5 and distribution tube 6 with the upper edge of the upper area 1a. Suction of pump 5 is provided by inlet CD for the supply of carbon dioxide. Collecting tank 4 is equipped by an air supply line AA for aeration of the suspension. Part of the module are formed by the diffusing area 3 for removal of oxygen from the algal suspension, collecting tank 4 and pump 5 for circulation of the suspension during cultivation, and distributing tube 6 for distribution of the suspension on the cultivation area. The collecting tank 4 is placed below the end of the lowest, i.e., the fourth inclined cultivation area 1d.

In order to the required turbulence of the algal suspension, the mutual relationship of the following variables is optimized: roughness of the cultivation surface, slope of the cultivation area, thickness of the algal suspension layer.

Functional description the FIGURE: Pump 5 lifts suspension of algae from tank 4 into distributing tube 6, from which it flows out on cultivation area 1a. Cultivation area 1a of 1.7% slope is made of glass sheets having surface roughness $n=0.01$ $s^{-\frac{1}{3}}$.m. Suspension layer 6 mm thick flows at velocity 50–60 cm.$s^{-1}$ along the sheets into the connecting channel 2 where the suspension is supplied with carbon dioxide. The suspension is transported by the channel to the next inclined cultivation are 1b, which is, with respect to the foregoing area, inclined in the opposite direction. From area 1b the suspension flows on diffusing area 3 and from here into collecting tank 4 and the whole process is continuously repeated Except for diffusion of the suspension during cultivation, diffusing area or member 3 is being used, by simple tipping over, for draining of water outside the tank during rain (RW).

For cultivation, a suitable production strain of algae is used, being precultivated in a laboratory bioreactor. Production cultivation in the outdoor bioreactor is carried out in inorganic nutrient solution, either semicontinuously or in a fed-batch regime. In semicontinuous regime the culture is being grown up to the harvesting concentration of about 20–30 g of algal dry weight per liter of nutrient solution. Then, about 50% of the biomass is harvested so that the concentration of algae in the nutrient solution is lowered to 10–15 g dry weight.$l^{-1}$. Within the limits of the above given concentration of algae the whole process of semicontinuous cultivation and of harvest is repeated.

In the case of fed-batch cultivation, the algae are grown up to the concentration 20–30 g.$l^{-1}$. Then, all biomass is harvested. About 5% of the harvested biomass is used, after washing, as inoculum in a new cultivation cycle. In both described cultivation regimes the nutrients consumed by the algae are added daily.

Industrial Utilization

The process according to the patent can be utilized for large-scale solar cultivation of microalgae and of blue-green algae.

We claim:

1. A bioreactor for an outdoor thin layer cultivation of algae in a suspension of algae, consisting essentially of:

only one upper elongated and featureless cultivation area (1a) with an upper end and a lower end, the upper cultivation area having a first upper surface for receiving a flow of algae suspension, the first upper surface having an inclination and coefficient of roughness;

only one lower elongated and featureless cultivation are (1b) extending substantially parallel to the upper cultivation area, the lower cultivation area having an upper end and a lower end, the lower cultivation area having a second upper surface for receiving a flow of algae suspension, the second upper surface having an inclination and coefficient of roughness;

the inclinations of the upper and lower cultivation areas being opposite to each other and each being 1.1 to 2.5%, the coefficients of roughness each being 0.005 to 0.150 $m^{-\frac{1}{3}}$. s;

a channel (2) connecting the lower end of the upper cultivation area to the upper end of the lower cultivation area;

a collecting tank (4) below the lower end of the lower cultivation area;

pump means for returning algae suspension from the tank to the upper end of the upper cultivation area, the pump means supplying a layer of algae suspension along the first and second surfaces at a thickness of 5 to 18 mm and a flow velocity of 30 to 150 cm·$s^{-1}$ for moving the suspension along the surfaces under turbulence which is cause by the inclination and the coefficient of roughness, the suspension moving from the upper to the lower cultivation areas through the channel; and means for saturating the suspension with carbon dioxide by supplying carbon dioxide into the channel, the suspension being enriched with nutrients for the algae.

2. A bioreactor according to claim 1, including a diffusing member between the lower end of the lower cultivation area and an upper open end of the collecting tank for receiving rainwater and for receiving suspension from the lower end of the lower cultivation area.

3. A bioreactor according to claim 2, including a perforated pipe extending into the channel for supplying carbon dioxide for saturating the suspension in the channel with carbon diode.

4. A bioreactor according to claim 3, including means for supplying additional carbon dioxide into the pump means.

5. A bioreactor according to claim 4, wherein the pump means comprises a pump, a distribution pipe extending along the upper end of the upper cultivation area, the pump being connected to the distribution pipe.

6. A process for outdoor thin layer cultivation of algae in a suspension of algae, the process comprising:

providing a bioreactor which consists essentially of only one upper elongated and featureless cultivation area (1a) with an upper end and a lower end, the upper cultivation area having a first upper surface for receiving a flow of algae suspension, the first upper surface having an inclination and coefficient of roughness; and only one lower elongated and featureless cultivation area (1b) extending substantially parallel to the upper cultivation area, the lower cultivation area having an upper end and a lower end, the lower cultivation area having a second upper surface for receiving a flow of algae suspension, the second upper surface having an inclination and coefficient of roughness, the inclinations of the upper and lower cultivation areas being opposite to each other and each being 1.1 to 2.5%, the coefficients of roughness each being 0.005 to 0.150 $m^{-1/3} \cdot s$; a channel (2) connecting the lower end of the upper cultivation area to the upper end of the lower cultivation area; a collecting tank (4) below the lower end of the lower cultivation area; and pump means for returning algae suspension from the tank to the upper end of the upper cultivation area;

supplying a layer of algae suspension along the first and second surfaces at a thickness of 5 to 18 mm and a flow velocity of 30 to 150 $cm \cdot s^{-1}$ for moving the suspension along the surfaces under turbulence which is cause by the inclination and the coefficient of roughness, the suspension moving from the upper to the lower cultivation areas through the channel, the algae suspension being enriched with nutrients;

saturating the suspension with carbon dioxide by supplying carbon dioxide into the channel; and using the pump means to return the suspension from the tank to the upper cultivation area.

7. A process according to claim 6, including providing a diffusing member (3) below the lower end of the lower cultivation area for receiving suspension therefrom, and above the collecting tank, the diffusing member being placed for receiving rainwater.

8. A process according to claim 7, including tilting the diffusing member for adjusting an amount of rainwater being sprayed onto the suspension before it reaches the collecting tank.

9. A process according to claim 8, including supplying additional carbon dioxide into the suspension between the collecting tank and the pumping means.

* * * * *